(12) United States Patent
Yasumoto et al.

(10) Patent No.: US 7,745,191 B2
(45) Date of Patent: Jun. 29, 2010

(54) METHOD OF PRODUCING HETERODIMER DERIVATIVE OF PROTEIN PHOSPHATASE TYPE 2A ENZYME

(75) Inventors: Takeshi Yasumoto, Uruma (JP); Tsuyoshi Ikehara, Uruma (JP); Fukiko Shinjyo, Uruma (JP)

(73) Assignee: Tropical Technology Center Ltd., Uruma-shi (JP)

( * ) Notice: Subject to any disclaimer, the term of this patent is extended or adjusted under 35 U.S.C. 154(b) by 111 days.

(21) Appl. No.: 12/094,067

(22) PCT Filed: Nov. 16, 2005

(86) PCT No.: PCT/JP2005/021011

§ 371 (c)(1),
(2), (4) Date: May 16, 2008

(87) PCT Pub. No.: WO2007/057949

PCT Pub. Date: May 24, 2007

(65) Prior Publication Data

US 2009/0093018 A1    Apr. 9, 2009

(51) Int. Cl.
*C12N 9/16* (2006.01)
(52) U.S. Cl. ..................................................... 435/196
(58) Field of Classification Search .................. None
See application file for complete search history.

(56) References Cited

FOREIGN PATENT DOCUMENTS

JP    2003 250598    9/2003

WO    WO 2006/048923 A1    5/2006

OTHER PUBLICATIONS

Ikehara et al. Baculovirus expression, purification, and characterization of human protein phosphatase 2A catalytic subunits alpha and beta. Protein Expression and Purification 45 (2206) 150-156 (available on line Jul. 1, 2005).*
Myles T. et al., "Active-site mutations impairing the catalytic function of the catalytic subunit of human protein phosphatase 2A permit baculovirus-mediated overexpression in insect cells", Biochem. J., vol. 657, p. 225 (2001).
S. Reuveny, et al., "Effect of temperature and oxygen on cell growth and recombinant protein production in insect cell cultures", Applied Microbiology and Biotechnology, Springer Verlag, vol. 38, No. 5, XP000876997, Feb. 1, 1993, pp. 619-623.
Michael Donaldson, et al., "Glycosylation of a Recombinant Protein in the Tn5B1-4 Insect Cell Line: Influence of Ammonia, Time of Harvest, Temperature, and Dissolved Oxygen", Biotechnology and Bioengineering, vol. 63, No. 3, XP009118107, May 5, 1999, pp. 255-262.

* cited by examiner

*Primary Examiner*—Nashaat T Nashed
(74) *Attorney, Agent, or Firm*—Oblon, Spivak, McClelland, Maier & Neustadt, L.L.P.

(57) ABSTRACT

The purpose of the invention is to provide an activated protein phosphatase 2A (PP2A) in large quantities with high purity by a genetic engineering and to provide a method for producing a heterodimer derivative of PP2A which comprises infecting insect cultured cells with a baculovirus in which a cDNA encoding the catalytic subunit of PP2A carrying a first tag is integrated together with another baculovirus in which a cDNA encoding the A subunit of PP2A carrying a second tag is integrated, incubating the infected cells, disrupting the incubated cells to obtain a disrupted cell suspension, and then purifying the disrupted cell suspension with a solid phase carrying a substance capable of binding to the first tag and another solid phase carrying a substance capable of binding to the second tag, characterized in that the insect cells infected with the baculovirus are incubated at a temperature of from 18 to 22° C.

20 Claims, 4 Drawing Sheets

METHOD OF PRODUCING HETERODIMER DERIVATIVE OF PROTEIN PHOSPHATASE TYPE 2A ENZYME

CROSS-REFERENCE TO RELATED APPLICATIONS

The present application is a 35 U.S.C. §371 National Stage patent application of International patent application PCT/JP05/021011, filed on Nov. 16, 2005.

BACKGROUND OF THE INVENTION

1. Field of the Invention

The present invention relates to a method for producing heterodimer derivatives of protein phosphatase 2A (hereinafter abbreviated to as "PP2A"). More particularly, it relates to a method for production of a large quantity of heterodimer derivatives of PP2A consisting of the catalytic subunit and A subunit of PP2A, each carrying a tag, from which derivatives a highly pure PP2A can be prepared.

2. Description of the Related Art

PP2A is one of the most basic enzymes among hydrolases by which the phosphate groups attached to serine/threonine residues in a protein are hydrolyzed, and is formed as a complex of trimer in which a catalytic subunit termed PP2Ac is linked to an A subunit and a B subunit. Among these subunits, the catalytic subunit and the A subunit include two forms of α-isoform and β-isoform.

The PP2A which plays an important role in signal transduction in vivo is in big demand as a biochemical reagent and has come onto the market at a high price. In addition, in recent years, there is a need as a constitutive reagent for a convenient kit for measurement of toxic components, okadaic acids, accumulated in marine Bivalvia, or blue-green algal toxins (microcystins, nodularins), which are subjects to regulation as poisonous ingredients in lakes and marshes.

At present, as for PP2A used for the above-mentioned objects, no one but a heterodimer of the A subunit and the catalytic subunit has been known, which is referred to as PP2A and prepared from the human blood corpuscles.

The PP2A purified from the human blood corpuscles, however, is very expensive because of complicated purification process and difficulty of large-scale purification since it is separated from animal tissues. In addition, there was a problem in using the resulting PP2A as a biochemical reagent, since it is per se not likely to be sufficient in purity. Further, there was another problem that a large quantity of pure PP2A was unable to be produced at low cost or with easiness for the basic research, making it difficult to achieve research necessary for elucidation of a diversity of life process involving PP2A.

The present inventors previously studied a method for producing PP2A and found that in producing the intended catalytic subunit and A subunit of PP2A by a genetic engineering procedure using a baculovirus, attachment of a tag to the respective subunits allows easy separation from other proteins to obtain the subunits in a highly pure state. The inventors further found that production of the catalytic subunit and A subunit of PP2A carrying respectively different tags in the same cultured cells obtained a heterodimer of PP2A consisting of the catalytic subunit and A subunit respectively carrying different tags, and that use of these two tags possessed by these subunits allowed easy purification of the intended heterodimer only. A patent application was filed based on these findings.

When a baculoviral expression system was used, however, there was another problem that the rate of PP2A expressed as an insoluble protein was higher than that as a soluble protein, thereby decreasing the rate of PP2A to be purified, though the rate of expression was high.

BRIEF SUMMARY OF THE INVENTION

Problem to be Solved by the Invention

Thus, an object of the present invention is to provide a means for solving the problem that the rate of PP2A to be purified is low when a baculovirus as an expression system is used.

DETAILED DESCRIPTION OF THE INVENTION

Means for Solving the Problems

Figure 1:
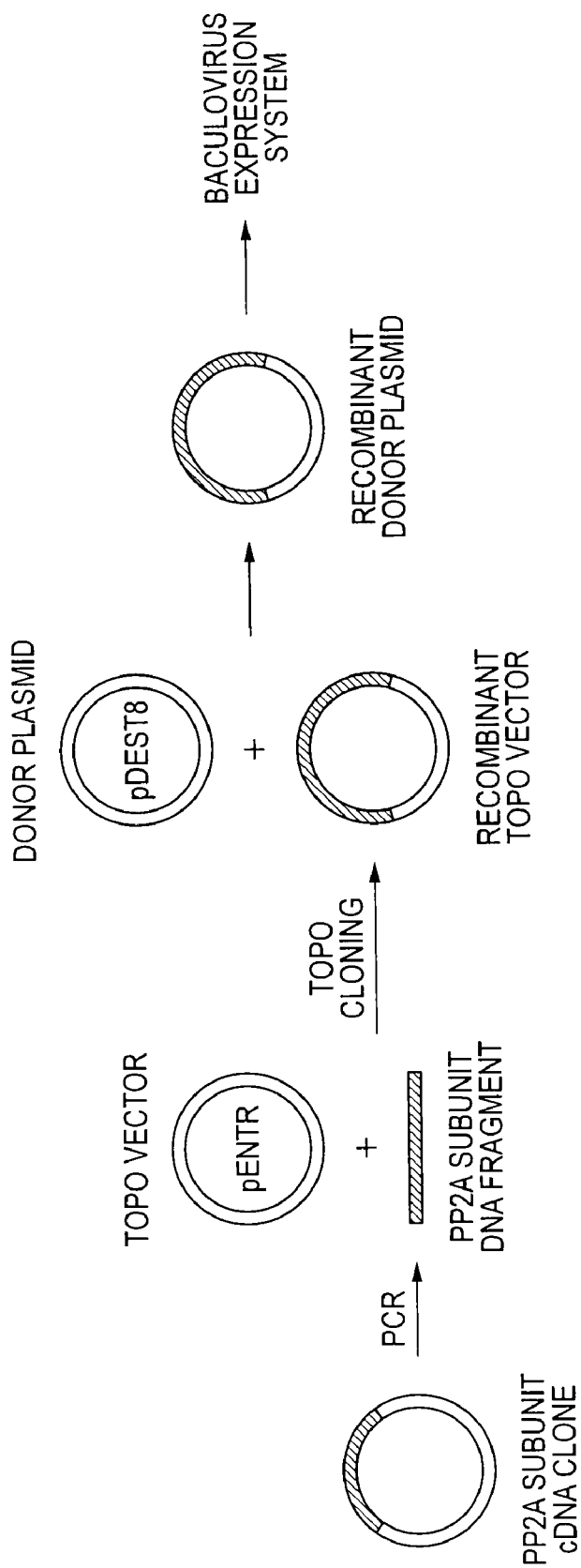
FIG. 1 shows the first half of the method of the invention.

In order to solve the above problems, the present inventors have assiduously studied the culture condition of insect cells particularly after infection with baculovirus, and found that the soluble PP2A to be purified was markedly increased in quantities when the insect cells were incubated at a temperature lower than that employed in a usual culture condition. Thus, the invention was completed.

The invention provides a method for producing a heterodimer derivative of protein phosphatase 2A (PP2A) which comprises the steps of infecting insect cultured cells with a baculovirus in which a cDNA encoding the catalytic subunit of PP2A carrying a first tag is integrated together with another baculovirus in which a cDNA encoding the A subunit of PP2A carrying a second tag is integrated, incubating the infected cells, then disrupting the incubated cells to obtain a disrupted cell suspension, and then purifying the disrupted cell suspension with a solid phase carrying a substance capable of binding to the first tag and another solid phase carrying a substance capable of binding to the second tag, characterized in that the insect cells infected with the baculovirus are incubated at a temperature of from 16 to 22° C.

The invention also provides a method for producing a catalytic subunit derivative of PP2A which comprises the steps of infecting insect cultured cells with a baculovirus in which a cDNA encoding the catalytic subunit of PP2A carrying a tag is integrated, incubating the infected cells, disrupting the incubated cells to obtain a disrupted cell suspension, and then purifying the disrupted cell suspension with a solid phase carrying a substance capable of binding to the tag, characterized in that the insect cells infected with the baculovirus are incubated at a temperature of from 16 to 22° C.

In addition, the invention provides a method for producing an A subunit derivative of PP2A which comprises the steps of infecting insect cultured cells with a baculovirus in which a cDNA encoding the A subunit of PP2A carrying a tag is integrated, incubating the infected cells, disrupting the incubated cells to obtain a disrupted cell suspension, and then purifying the disrupted cell suspension with a solid phase carrying a substance capable of binding to the tag, characterized in that the insect cells infected with the baculovirus are incubated at a temperature of from 16 to 22° C.

EFFECT OF THE INVENTION

According to the invention, PP2A heterodimer derivatives having the PP2A activity can be produced conveniently in large quantities with high purity not through complicated extraction and purification steps of the conventional techniques.

Therefore, the PP2A heterodimer derivatives obtained in the invention can widely be utilized as PP2A of which the demand as a biochemical reagent is expected to increase. In addition, it is expected to be utilized in development of a convenient kit for measurement of okadaic acids and the like.

BEST MODE FOR CARRYING OUT THE INVENTION

The term "derivative(s)" as used herein means that a tag is mainly attached to an original compound. For example, a PP2A catalytic subunit carrying a polyhistidine tag, FLAG tag, GST tag, HA tag, or the like is defined as a PP2A catalytic subunit derivative.

In carrying out the invention, it is necessary to first obtain a tagged catalytic subunit of PP2A and a cDNA encoding an A subunit of PP2A. The preferred origin of the cDNA includes, but not particularly limited to, animals such as human, mouse, rat, and the like, and cDNA of human origin is particularly preferred.

In the cDNA, a tagged catalytic subunit of PP2A can be obtained, for example, by preparing a plasmid clone containing a cDNA encoding α- or β-isoforms of the PP2A catalytic subunit (PP2Ac) and a primer corresponding to the tag, and carrying out PCR using the plasmid clone as template. A cDNA encoding the tagged A subunit of PP2A may be obtained in the same way as above by PCR using a plasmid clone containing a cDNA encoding the A subunit of PP2A and a primer corresponding to the tag. In each of the above-mentioned subunits, it is preferred for the tag to be attached to the respective N-terminals.

The resulting cDNAs as mentioned above, which encode a tagged PP2A catalytic subunit or a tagged PP2A A subunit, are respectively integrated into a baculovirus, which is then introduced together into insect cultured cells; the cells are incubated, from which the intended PP2A heterodimer derivative is obtained. In this invention, it is important to carry out incubation of the insect cultured cells infected with baculovirus at a lower temperature than usual incubation temperatures (about 27° C.); thus, the amount of PP2A heterodimer derivative expressed is markedly increased. Specifically, the cells are incubated at around 16 to 22° C., and more preferably at around 18 to 20° C.

According to the invention, the PP2A heterodimer derivatives can be produced by carrying out a process comprising the following steps:

(1) Integrating individually cDNAs encoding a catalytic subunit and an A subunit of PP2A into cloning vectors;

(2) Integrating individually the cDNAs encoding the respective subunits in the above respective cloning vectors into recombinant donor plasmids for use in a baculovirus expression system;

(3) Integrating individually the cDNAs encoding the respective subunits by site-specific transposition from the above recombinant donor plasmids into a baculovirus shuttle vector (Bacmid);

(4) Preparing individually baculovirus in which the cDNA encoding each subunit is integrated, from the above baculovirus shuttle vector;

(5) Transfecting the resulting respective baculovirus together into insect cultured cells to express the PP2A heterodimer derivative, and incubating the cells at a temperature lower than the above-mentioned usual incubation temperature; and (6) Purifying the expressed PP2A heterodimer in two steps.

Figure 2:
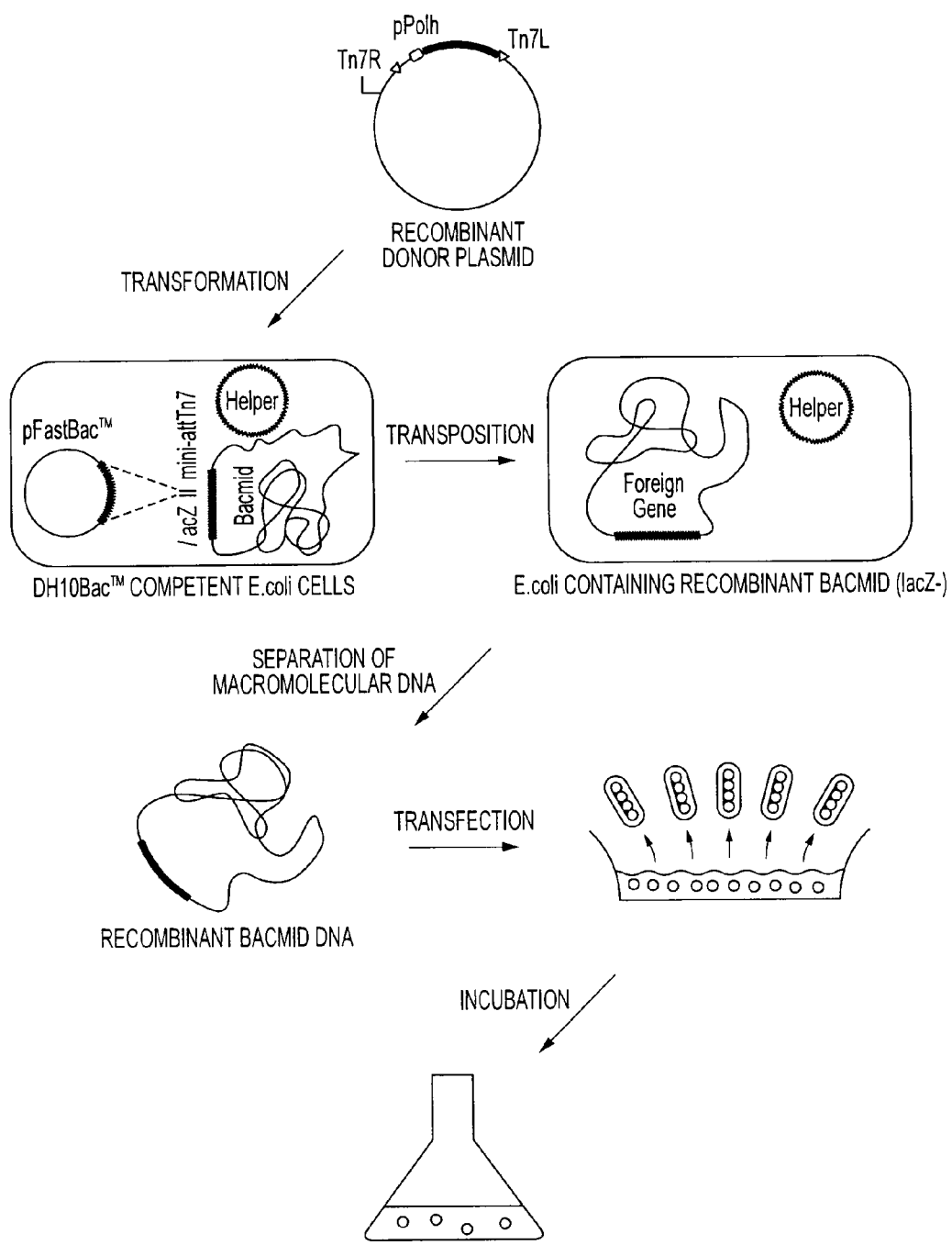
FIG. 2 shows the latter half of the method of the invention (except the purification step).

In the above-mentioned process, the steps (1) and (2) are depicted in FIG. 1, and the steps (3) to (5) in FIG. 2.

As for the cloning vectors used in the above step (1), TOPO vector and the like may be used. As for the donor plasmids used in the above step (2), pDEST8 and the like may be used. Further, in carrying out the steps (3) and (4), for example, a commercially available expression system, such as Bac-to-Bac baculovirus, may be used. Further, as for the host cells to be infected with a baculovirus containing a cDNA encoding each subunit, cells of armyworm or silkworm are utilized, and particularly Sf9 cell, Sf21 cell, and High Five cell are preferred.

The invention is characterized in that the insect cultured cells infected with a baculovirus are incubated at a lower temperature than the usual incubation temperature (27° C.) in the above-mentioned step (5), that is, at a temperature of around 16 to 22° C., preferably at around 18 to 20° C. At such a temperature, the intended PP2A heterodimer derivative can be produced in much higher yield, though it is necessary to somewhat prolong the incubation period compared with the case conducted at a usual incubation temperature.

Thus, the PP2A heterodimer derivative produced in the incubated cells can be isolated from the disrupted cell suspension obtained from the incubated cells by disruption. In carrying out disruption of the incubated cells, such a procedure as ultrasonication or homogenization may be employed. Thus resulting disrupted cell suspension is subjected to separation from other contaminants in the step (6) using the tag attached to each subunit. Specifically, the catalytic subunit and A subunit of PP2A carry respectively distinct tags; thus, the suspension is sequentially brought into contact with the respective solid phases carrying the substances capable of binding to such tags, to obtain the PP2A heterodimer derivative only.

In separation with these two tags, for example, when the tag attached to the PP2A catalytic subunit is polyhistidine tag and the tag attached to the A subunit is FLAG tag, the cells are disrupted by centrifugation of the suspension, and then the resulting disrupted cell suspension is brought into contact with a solid phase carrying a substance capable of binding to the polyhistidine tag, such as Ni-carrying solid phase. As for the solid phase, for example, agarose and the like are utilized; the incubated suspension may be contacted with solid phases in either batchwise or passing-through way.

Subsequently, the solid phase with which the disrupted cell suspension has been contacted is washed with a suitable solvent, and then treated with a processing solvent capable of cleaving the linkage with the polyhistidine tag to obtain an eluate. When a target for binding to polyhistidine is Ni, for example, 100-250 mM of imidazole and the like are employed as the processing solvent.

Further, the above eluate is brought into contact with a solid phase carrying a substance binding to FLAG tag. The substance binding to the FLAG tag includes anti-FLAG M2 monoclonal antibody and the like; the solid phase employed and the way of contact may be the same as mentioned above.

Thereafter, the solid phase which has been contacted with the eluate is washed well with a suitable solvent, and then treated with a processing solvent capable of cleaving the linkage with the FLAG tag to obtain an eluate. As the processing solvent, 0.2 mg/mL of FLAG peptide is employed, for example.

On the other hand, when the tag attached to the catalytic subunit of PP2A is HA tag and the tag attached to the A subunit is GST tag, the disrupted cell suspension obtained in the same manner as above is brought into contact with a substance capable of binding to HA tag, for example, solid phase carrying an anti-HA antibody. As for the solid phase, for example, agarose and the like are utilized; and the contact of the solid phase with the incubated suspension may be achieved in either batchwise or passing-through way.

Thereafter, the solid phase which has been contacted with the disrupted cell suspension is washed with a suitable solvent, and then treated with a processing solvent capable of cleaving the linkage with the HA tag to obtain an eluate. As the processing solvent, when a target for binding to the HA tag is an anti-HA antibody, 1 mg/mL of HA peptide and the like is employed.

Further, the above eluate is brought into contact with a solid phase carrying a substance binding to GST tag. The substance binding to the GST tag includes glutathione and the like; the solid phase employed and the way of contact may be the same as mentioned above.

Thereafter, the solid phase which has been contacted with the eluate is washed well with a suitable solvent, and then treated with a processing solvent capable of cleaving the linkage with the GST tag to obtain an eluate. As the processing reagent, 5-10 mM of reduced glutathione is employed, for example.

Thus resulting eluate only contains a PP2A heterodimer derivative as an organic compound, and it can be utilized as a reagent and the like on its own or after lyophilization. That is, since the PP2A heterodimer derivative is purified by a two-step process, when a polyhistidine tag and a FLAG tag are used as tags, for example, only the substances carrying both tags are left in the product. The PP2A heterodimer derivative is the only substance satisfying such a requirement in the method of the invention.

Thus, a PP2A heterodimer derivative having very high purity can be obtained by the above process.

In this connection, the PP2A catalytic subunit derivative can be produced by infecting the cells of an insect independently with a baculovirus in which a cDNA encoding a tagged catalytic subunit is integrated in the step (5), and then carrying out the purification in the step (6) using the tag attached to the catalytic subunit at one-stage; but otherwise the above-mentioned steps (1) to (6) may be carried out independently.

EXAMPLES

The invention is explained in detail by the following examples which are not intended to limit the invention. In addition, since it is apparent that an embodiment of the method as described in Examples can be modified, such modification should not be interpreted to depart from the scope of the invention, and all of modifications considered to be obvious fall within the scope of Claims of the invention.

Example 1

Plasmid clones containing cDNAs respectively encoding α- and β-isoforms of human PP2A catalytic subunit (PP2Ac) (purchased from Invitrogen; Clone ID 3607862 and 4454972) were used as templates, and DNA fragments encoding the catalytic subunits carrying a polyhistidine tag (His-PP2Acα and His-PP2Acβ) were amplified by PCR.

PCR was conducted in the following condition, where the following primers were employed.

[Condition of PCR]
The following step (1) was conducted in one cycle, then (2) in 25 cycles, and finally (3) in one cycle.
(1) 94° C., 2 min.
(2) 94° C., 30 sec.
↓
55° C., 1 min.
↓
72° C., 2 min.
(3) 72° C., 2 min.
[Primers Employed]

```
Primer 1 (for α-isoform):
5'-CACCATGCATCACCATCACCATCACCATCACGACGAGAAGGTGTTCA

CCAAG-3'
(SEQ ID NO: 1)

Primer 2 (for α-isoform):
5'-TTATTACAGGAAGTAGTCTGGG-3'
(SEQ ID NO: 2)

Primer 3 (for β-isoform):
5'-CACCATGCATCACCATCACCATCACCATCACGACGACAAGGCGTTCA

CCAAG-3'
(SEQ ID NO: 3)

Primer 4 (for β-isoform):
5'-TTATTATAGGAAGTAGTCTGGG-3'
(SEQ ID NO: 4)
```

The DNA fragments amplified by PCR were sub-cloned into the pENTR/SD/D-TOPO vector using "pENTR Directional TOPO Cloning Kits" (Invitrogen). The DNA sequences and direction of the sub-cloned DNA fragments were investigated and confirmed using ABI PRISM 3100 Genetic Analyzer (Applied Biosystem).

The sub-cloned DNA fragments were further inserted into "Gateway pDESTS Vector" (Invitrogen) using a "Baculovirus Expression System with Gateway Technology kit" (Invitrogen) to obtain recombinant donor plasmids.

Using the prepared recombinant donor plasmids and a Bac-to-Bac baculovirus expression system, recombinant baculovirus shuttle vectors (Bacmid) were prepared, and then recombinant baculoviruses were produced utilizing insect cultured cells (Sf9 cells; purchased from Invitrogen).

Example 2

Plasmid clones containing cDNAs encoding a human PP2A A subunit (PR65α/Aα) (purchased from Invitrogen; Clone ID IOH13670) were used as templates, and DNA fragments encoding the A subunit carrying FLAG tag (FLAG-PR65α/Aα) were amplified by PCR.

PCR was conducted in the following condition, where the following primers were employed.

[Condition of PCR]
The following step (1) was conducted in one cycle, then (2) in 25 cycles, and finally (3) in one cycle.
(1) 94° C., 2 min.
(2) 94° C., 30 sec.
↓

55° C., 1 min.
↓
72° C., 3 min.
(3) 72° C., 2 min.
[Primers Employed]

Primer 5
5'-CACCATGGACTACAAGGATGACGATGACAAGGCGGCGGCCGACGGCG
ACGAC-3'
(SEQ ID NO: 5)

Primer 6
5'-TTATCAGGCGAGAGACAGAAC-3'
(SEQ ID NO: 6)

In the same manner as in Example 1, the DNA fragments amplified by PCR were sub-cloned into the pENTR/SD/D-TOPO vectors to obtain the recombinant donor plasmids, the recombinant baculovirus shuttle vectors (Bacmid) were prepared, and the recombinant baculoviruses were produced utilizing insect cultured cells, thereby obtaining 1.5 mL of culture supernatant containing the recombinant baculoviruses.

Example 3

The recombinant baculoviruses in which cDNAs encoding the PP2A catalytic subunits were integrated were infected to 200 mL of High Five cells ($2 \times 10^6$ cells/mL; 1 L spinner flask) and incubated at 19° C. for 4 days. After incubation, the cells were recovered, from which recombinant proteins were purified according to the following way.

The recovered cells re-suspended in PBS were centrifuged to collect the cells and remove the supernatant, and the cells thus collected were re-suspended in 20 mL of Buffer A (20 mM Tris-HCl, 2 mM EGTA, 0.5 mM benzamidine, 0.5 mM DTT, 10% glycerol). The cells in the suspension were disrupted by ultrasonication, and centrifuged with a small-size cooled centrifuge (15,000 rpm, 20 min., 4° C.) to recover the supernatant.

The resulting supernatant (5 μL) was applied to SDS-PAGE, and the expression of PP2A catalytic subunit was confirmed by Western blotting. The supernatant containing the PP2A catalytic subunit expressed as a soluble protein was mixed and quickly agitated with 5 parts by volume of ethanol, and centrifuged (4200×g, 15 min).

After centrifugation, the supernatant was removed, and the precipitate was suspended in 20 mL of Buffer A. This suspension was centrifuged (10,000×g, 20 min., 4° C.) to recover the supernatant, 800 μL of Ni-NTA agarose (QIAGEN) equilibrated with Buffer A was added to the supernatant thus obtained, and the mixture was stirred moderately at 4° C. for 1 hour.

After a lapse of 1 hour, Ni-NTA agarose was recovered and washed with Buffer A, and then 2.4 mL of eluate (Buffer A containing 250 mM imidazole) was added thereto, and the mixture was stirred moderately at 4° C. for 30 minutes. After a lapse of 30 minutes, the eluate was carefully recovered so that Ni-NTA agarose is not admixed.

By SDS-PAGE (0.2 μg of protein; 10% SDS-gel), the purified recombinant protein in the recovered eluate was confirmed. The activity of the purified protein was determined according to a method using p-nitrophenylphosphate as substrate (Takai et al. 1995, Biochem J. 306:657-665).

Figure 3:
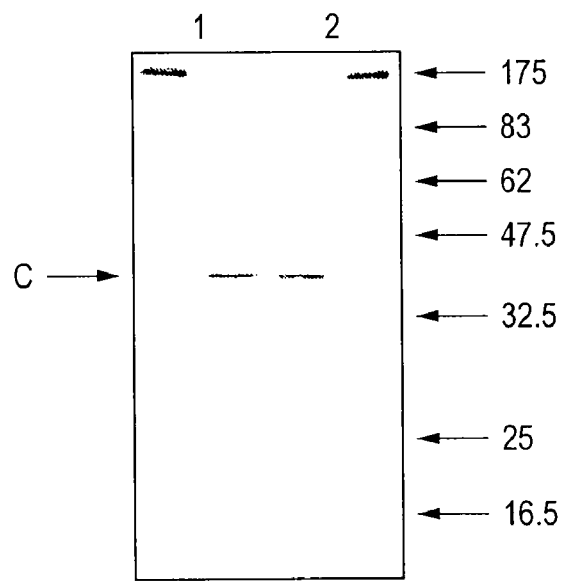
FIG. 3 shows the results (photograph) of SDS-PAGE conducted for the tagged catalytic subunit of PP2A in Example 3.
Figure 4:
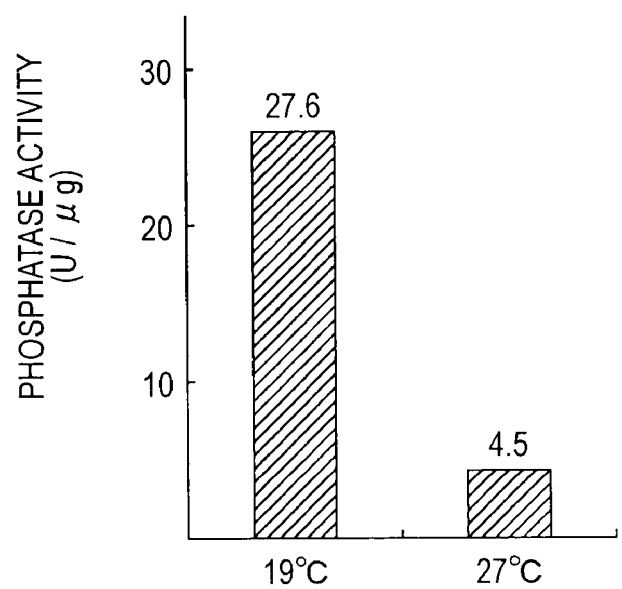
FIG. 4 shows the activity of the tagged catalytic subunit of PP2A in Example 3 to p-nitrophenylphosphate.

The result of SDS-PAGE is shown in FIG. 3, and the activity to p-nitrophenylphosphate is shown in FIG. 4, respectively. In both figures, the term "27° C." indicates the tagged catalytic unit of PP2A (comparative example), which was prepared in the same manner as in Example 3 except that the cells infected with the recombinant baculovirus was incubated at 27° C. for 3 days. In FIG. 3, the both end side lanes indicate a marker, the 2nd lane from left indicates the tagged catalytic unit of PP2A prepared by incubation at 27° C., and the 3rd lane from left indicates the tagged catalytic unit of PP2A prepared by incubation at 19° C.

FIG. 3 shows that the tagged catalytic unit of PP2A prepared by incubation at 19° C. can be obtained with lower production of substances other than the intended compound. The result of FIG. 4 shows that change of the incubation temperature from 27° C. to 19° C. for the recombinant baculovirus-infected cells enhanced 6 times or more the activity of the tagged catalytic unit of PP2A. In this connection, the total yield of proteins was 240 μg/$4 \times 10^8$ High Five cells when incubation was conducted at 19° C., while the total yield of proteins was 88 μg/$4 \times 10^8$ High Five cells when incubation was conducted at 27° C.

Example 4

(1) For the recombinant baculoviruses prepared in Example 2, the amplification and infection with the virus was conducted, the infected cells were recovered, and the recombinant protein was purified in the same manner as in Example 3 except that $2 \times 10^7$ cells/mL of cells were used. The recovered cells were washed with PBS in the same manner as in Example 3, homogenized, and then centrifuged to obtain a supernatant. The resulting supernatant was treated with 40 μL of anti-FLAG M2 affinity gel (SIGMA) equilibrated with Buffer A, and stirred moderately at 4° C. for 1 hour. After a lapse of 1 hour, the anti-FLAG M2 affinity gel was recovered, washed with Buffer A, added 120 μL of eluate (Buffer A containing 0.2 mg/mL of FLAG peptide), and stirred moderately at 4° C. for 30 minutes. After a lapse of 30 minutes, the eluate was carefully recovered so that the anti-FLAG M2 affinity gel is not admixed. By SDS-PAGE, the purified recombinant protein in the recovered eluate was confirmed.

(2) After confirmation of purification of the catalytic subunit of human PP2A carrying a polyhistidine tag prepared in Example 3 and the A subunit of human PP2A carrying a FLAG tag prepared in Example 4 (1), High Five cells ($2 \times 10^7$) were co-infected with the viruses used in Examples 3 and 4, incubated at 19° C. for 4 days, recovered, and used for purification of a heterodimer (His-PP2Acα/FLAG-PR65α and His-PP2Acβ/FLAG-PR65α) recombinant proteins. Detail of purification method is as follows.

First, the cells recovered in the same manner as in Example 3 were washed with PBS, homogenized, and then centrifuged to obtain a supernatant. The resulting supernatant was treated with 40 μL of Ni-NTA agarose (QIAGEN) equilibrated with Buffer A, and the mixture was stirred moderately at 4° C. for 1 hour. After a lapse of 1 hour, Ni-NTA agarose was recovered and washed with Buffer A, 120 μL of eluate (Buffer A containing 250 mM imidazole) was added thereto, and the mixture was stirred moderately at 4° C. for 30 minutes. After a lapse of 30 minutes, the eluate was carefully recovered so that Ni-NTA agarose is not admixed. Through elution procedure repeated twice, the first eluate (120 μL) and the second eluate (120 μL) were combined to obtain 240 μL of eluate in total.

40 μL of anti-FLAG M2 affinity gel (SIGMA) equilibrated with Buffer A was added to the eluate, and the mixture was stirred moderately at 4° C. for 1 hour. After a lapse of 1 hour, the anti-FLAG M2 affinity gel was recovered and washed with Buffer A, 120 μL of an eluate (Buffer A containing 0.2 mg/mL of FLAG peptide) was added thereto, and the mixture was stirred moderately at 4° C. for 30 minutes. After a lapse of 30 minutes, the eluate is recovered carefully so that the anti-FLAG M2 affinity gel is not admixed. By SDS-PAGE, the purified recombinant protein in the recovered eluate was confirmed. The activity of the purified protein was determined according to a method using p-nitrophenylphosphate as substrate (Takai et al. 1995, Biochem J. 306:657-665).

Figure 5:
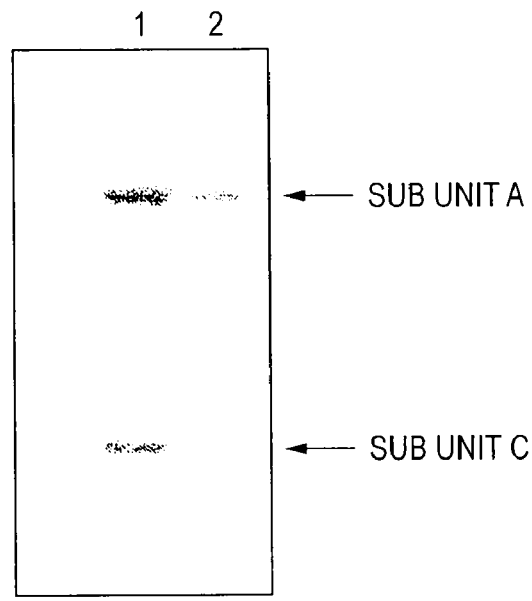
FIG. 5 shows the results (photograph) of SDS-PAGE conducted for the tagged heterodimer of PP2A in Example 3.
Figure 6:
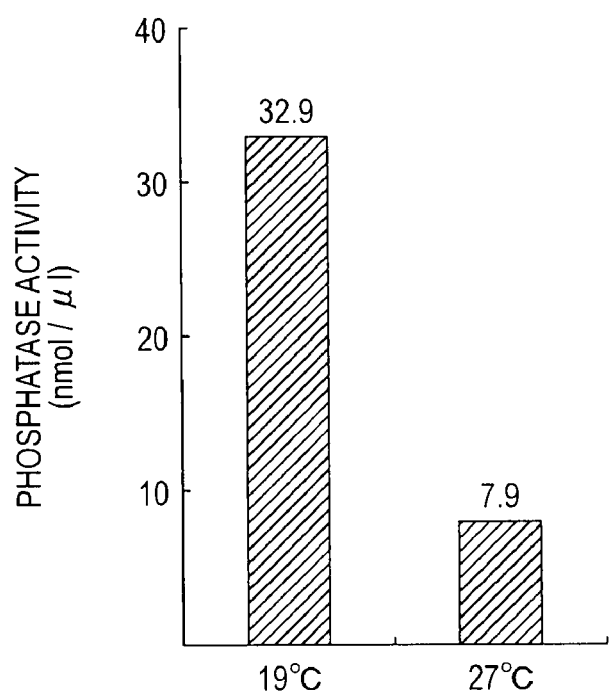
FIG. 6 shows the activity of the tagged heterodimer of PP2A in Example 3 to p-nitrophenylphosphate.

The tagged heterodimer (His-PP2Ac/FLAG-PR65) of the A subunit and catalytic subunit of PP2A purified in Example 4 were analyzed by SDS-PAGE. FIG. 5 shows the result. In the figure, the lane 1 indicates the tagged PP2A heterodimer prepared by incubation at 19° C., and the lane 2 indicates the PP2A heterodimer prepared by incubation at 27° C. FIG. 6 shows the results of investigation for the activity of the heterodimers to p-nitrophenylphosphate. These results show that according to the invention the tagged PP2A heterodimer can be prepared in a pure form in larger quantities than in the incubation conducted at a usual temperature of 27° C.

INDUSTRIAL APPLICABILITY

According to the method of the invention, it became possible to produce the tagged catalytic subunit of PP2A and the tagged heterodimer of PP2A A subunit and catlytic subunit in large quantities. Moreover, these products have very high purity, and can advantageously be used for the purpose of investigation of the inhibitory effect of okadaic acids, microcystin or nodularin on the PP2A activity. Further, the above heterodimers are able to bind to the B subunit of PP2A in an extract of animal cells, and expected to widely be applied in the field of basic research using PP2A.

The invention claimed is:

1. A method for producing a heterodimer derivative of protein phosphatase 2A (PP2A), comprising:
   infecting cultured insect cells with baculovirus that express a polypeptide comprising the catalytic subunit of PP2A and a first tag and that express a polypeptide comprising the A subunit of PP2A and a second tag;
   incubating the infected cells at a temperature ranging from 16° C. to 22° C.;
   disrupting the incubated cells to obtain a disrupted cell suspension; and then
   purifying the disrupted cell suspension with a solid phase carrying a substance capable of binding to the first tag and another solid phase carrying a substance capable of binding to the second tag, and recovering a heterodimer derivative of PP2A.

2. The method of claim 1, wherein the catalytic subunit of PP2A is a catalytic α-subunit or a catalytic β-subunit.

3. The method of claim 1, wherein
   the first tag is a polyhistidine tag, and
   the second tag is a FLAG tag.

4. The method of claim 1, wherein the first tag binds to nickel (Ni) ions and
   the second tag binds to an anti-FLAG M2 monoclonal antibody.

5. A method for producing a catalytic subunit derivative of PP2A, comprising:
   infecting insect cultured cells with a baculovirus containing cDNA encoding the catalytic subunit of PP2A carrying a tag;
   incubating the infected cells at a temperature ranging from 16° C. to 22° C.;
   disrupting the incubated cells to obtain a disrupted cell suspension; and then
   purifying the disrupted cell suspension with a solid phase carrying a substance capable of binding to the tag, thus recovering a catalytic subunit derivative of PP2A.

6. The method of claim 5, wherein the catalytic subunit of PP2A is a catalytic α-subunit or catalytic β-subunit.

7. The method of claim 5, wherein the tag is a polyhistidine tag.

8. The method of claim 5, wherein the substance capable of binding to the tag contains nickel (Ni) ions.

9. A method for producing a phosphatase 2A (PP2A) protein heterodimer derivative that comprises the catalytic subunit of PP2A and the A subunit of PP2A, comprising:
   infecting cultured insect cells with baculovirus encoding
      a polypeptide comprising the catalytic subunit and a first tag and
      a polypeptide comprising the A subunit of phosphatase 2A protein and a second tag;
   incubating the infected cells at a temperature of from 16 to 22° C.; and
   recovering a phosphatase 2A protein heterodimer derivative from said cells.

10. The method of claim 9, wherein the polypeptide comprising the catalytic subunit and the polypeptide comprising the A subunit have different tags.

11. The method of claim 9, wherein the polypeptide comprising the catalytic subunit comprises an α-isoform of the catalytic subunit.

12. The method of claim 9, wherein the polypeptide comprising the catalytic subunit comprises an β-isoform of the catalytic subunit.

13. The method of claim 9, wherein said PP2A heterodimer derivative is recovered by:
   disrupting the incubated cells to obtain a disrupted cell suspension;
   binding the polypeptide comprising the catalytic subunit and a first tag or, alternatively, binding the polypeptide comprising the A subunit and the second tag, to a first solid substrate,
   washing the solid substrate to remove unbound materials,
   eluting the bound materials by treating the solid substrate with a processing solvent that cleaves the linkage between the first or second tag and the first solid substrate,
   applying the eluted material to a second solid substrate that binds to the tag not bound by the first solid substrate,
   washing said second solid substrate to remove unbound material, and
   recovering a heterodimer derivative of PP2A.

14. The method of claim 9, wherein said first and second tag are selected from the group consisting of a polyhistidine tag, a FLAG tag, a GST tag, and an HA tag, provided the first and second tags are different.

15. The method of claim 9, wherein said cultured insect cells are selected from the group consisting of armyworm and silkworm cells.

16. The method of claim 9, wherein said cultured cells are selected from the group consisting of Sf9 cells, Sf21 cells, and High Five cells.

17. The method of claim 9, further comprising cleaving the linkage between the catalytic subunit and its tag and/or cleaving the linkage between the A subunit and its tag.

18. The method of claim 9, wherein the cultured insect cells are coinfected with a baculovirus encoding a polypeptide comprising the catalytic subunit and a first tag and a baculovirus encoding polypeptide comprising the A subunit of phosphatase 2A protein and a second tag.

19. The method of claim 18, wherein the cultured insect cells are independently infected with a baculovirus encoding a polypeptide comprising the catalytic subunit and a first tag and a baculovirus encoding polypeptide comprising the A subunit of phosphatase 2A protein and a second tag.

20. The method of claim 9, further comprising binding a PP2A beta subunit to said heterodimer derivative.

* * * * *

SEQUENCE LISTING

```
<160> NUMBER OF SEQ ID NOS: 6

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caccatgcat caccatcacc atcaccatca cgacgagaag gtgttcacca ag            52

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttattacagg aagtagtctg gg                                             22

<210> SEQ ID NO 3
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caccatgcat caccatcacc atcaccatca cgacgacaag gcgttcacca ag            52

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttattatagg aagtagtctg gg                                             22

<210> SEQ ID NO 5
<211> LENGTH: 52
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caccatggac tacaaggatg acgatgacaa ggcggcggcc gacggcgacg ac          52

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttatcaggcg agagacagaa c                                            21
```